US009402609B2

(12) United States Patent
Ramos Clamote

(10) Patent No.: US 9,402,609 B2
(45) Date of Patent: Aug. 2, 2016

(54) SURGICAL RETRACTING DEVICE AND METHOD FOR THE MANUFACTURE THEREOF

(75) Inventor: Joachim Ramos Clamote, Nice (FR)

(73) Assignee: SURGICAL PERSPECTIVE, Strasbourg (FR)

( * ) Notice: Subject to any disclaimer, the term of this patent is extended or adjusted under 35 U.S.C. 154(b) by 1087 days.

(21) Appl. No.: 13/203,097

(22) PCT Filed: Feb. 16, 2010

(86) PCT No.: PCT/EP2010/051906
§ 371 (c)(1),
(2), (4) Date: Dec. 7, 2011

(87) PCT Pub. No.: WO2010/097311
PCT Pub. Date: Sep. 2, 2010

(65) Prior Publication Data
US 2012/0078299 A1 Mar. 29, 2012

(30) Foreign Application Priority Data
Feb. 25, 2009 (FR) ..................... 09 51183

(51) Int. Cl.
*A61B 17/04* (2006.01)
*A61B 17/02* (2006.01)
*A61B 17/00* (2006.01)

(52) U.S. Cl.
CPC ......... *A61B 17/0218* (2013.01); *A61B 17/0281* (2013.01); *A61B 2017/00876* (2013.01); *A61B 2017/0404* (2013.01); *A61B 2017/0406* (2013.01); *A61B 2017/0417* (2013.01)

(58) Field of Classification Search
CPC ............... A61B 2017/0404; A61B 2017/0406; A61B 2017/0417; A61B 2017/0419; A61B 2017/0414; A61B 2017/0448; A61B 2017/0446; A61B 2017/0458; A61B 2017/0459
USPC ......................................... 606/232
See application file for complete search history.

(56) References Cited

U.S. PATENT DOCUMENTS 3,409,014 A * 11/1968 Shannon .................. 606/148
3,785,643 A * 1/1974 Rich ..................... A63B 67/10
473/575

(Continued)

FOREIGN PATENT DOCUMENTS

| EP | 1 159 919 A2 | 12/2001 |
| EP | 1 413 255 A1 | 4/2004 |
| EP | 1 894 529 A2 | 3/2008 |

OTHER PUBLICATIONS

International Search Report, dated Jun. 22, 2010, from corresponding PCT application.

*Primary Examiner* — Gregory Anderson
(74) *Attorney, Agent, or Firm* — Young & Thompson

(57) ABSTRACT

A surgical retracting device includes a linking element and support element, characterized in that the linking element is a thread (2) and in that support element (1) includes a first and second face and at least three holes in which the thread passes through (6, 7, 8), the support element (1) and thread (2) being connected by a first knot (18) on the first face (A) and by a second knot (19) on the second face (B). A process for manufacturing the aforementioned device is also described. The device is useful in surgical operations for retaining or retracting biological or synthetic tissue, in particular during mini-invasive operations.

14 Claims, 4 Drawing Sheets

(56) References Cited

U.S. PATENT DOCUMENTS

| | | |
|---|---|---|
| 6,506,197 B1 | 1/2003 | Rollero et al. |
| 2005/0251205 A1* | 11/2005 | Ewers et al. ............ 606/232 |
| 2006/0122608 A1 | 6/2006 | Fallin et al. |
| 2008/0071297 A1 | 3/2008 | Kohl et al. |
| 2008/0300618 A1 | 12/2008 | Gertner |
| 2009/0018655 A1* | 1/2009 | Brunelle et al. ........... 623/13.19 |

* cited by examiner

FIG. 9
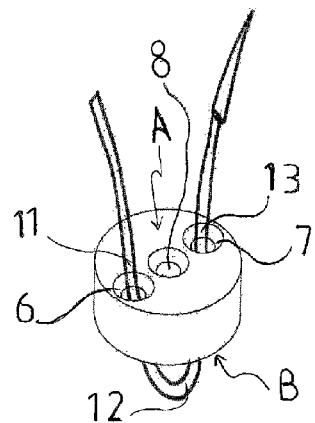
FIG. 10
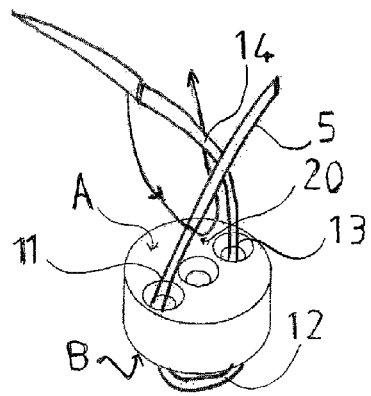
FIG. 11
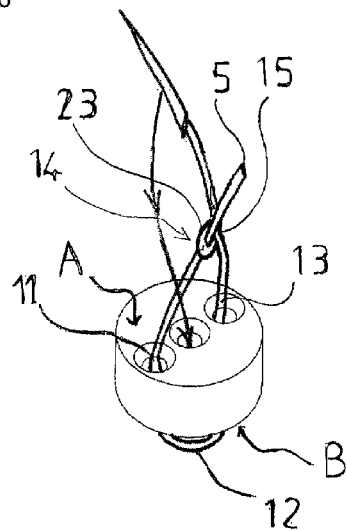
FIG. 12
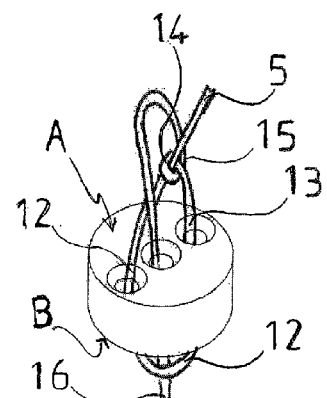
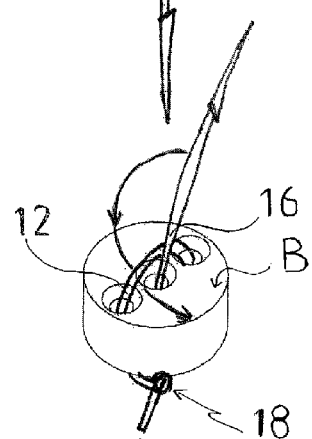
FIG. 13
FIG. 14
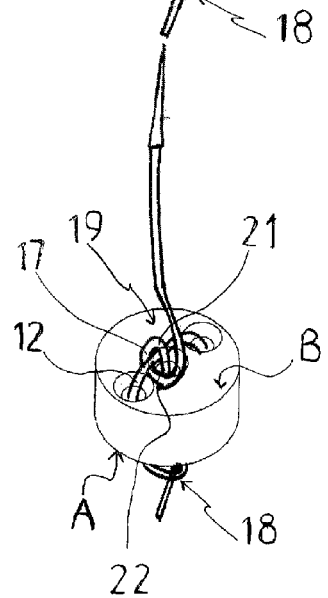

SURGICAL RETRACTING DEVICE AND METHOD FOR THE MANUFACTURE THEREOF

BACKGROUND OF THE INVENTION

1. Field of the Invention

The present invention concerns a surgical retracting device and its method of manufacture.

It will be of use during surgical operations to retain or retract biological or synthetic tissue, in particular in mini-invasive operations.

2. Description of the Related Art

During surgical operations, in particular laparoscopies, the surgeon's range of movements is limited. They use various instruments including thread with a pea to lift various organs from the zone to be operated on. This instrument consists of a thread placed on a needle and equipped with a pea at its other end. The pea is created manually by the surgeon before or during the operation using cotton or gauze. This type of small ball of gauze or cotton is pricked by the needle so as to be held on the thread. This thread equipped with a pea is used by passing the needle through the biological and/or synthetic tissue until the pea comes into contact with the tissue. The surgeon then pulls on the thread in order to retract the tissue.

An instrument such as described above has the main disadvantage of having to be made manually by the surgeon. This is time wasting and does not guarantee the reliability of the finished assembly. Another disadvantage is that the surgeon could be pricked when preparing this assembly.

Therefore, there is a need for a thread-with-pea type instrument that can manufactured industrially and reproducibly.

SUMMARY OF THE INVENTION

To this end, the present invention concerns a surgical device comprising a linking element such as a thread and a support element with at least three holes in which the thread passes through so as to attach the button and the thread by a first knot on a first face of the support element and a second knot on the second face of the support element. For instance, a button may be used as the support element.

This device according to the invention may be manufactured industrially based on a simple process. The surgical fixing device could then be marketed in a form that would enable its immediate use by the surgeon.

The support element and the linking element are joined so as to ensure the strength of the linking element. Indeed, the support element and the knots on the first and the second face are connected so as not to weaken the linking element.

According to a preferred embodiment, at least three through holes on the support element are aligned so as to limit the strain on the interlinking element and therefore the risk of it breaking.

Other goals and advantages will appear in the following description of a preferred but not restrictive embodiment of the invention.

First of all it has to be remembered that the invention concerns a surgical retracting device comprising an linking element and a support element characterised in that the linking element is a thread and that the support element comprises a first face, a second face and at least three through holes in which the thread passes through, the support element and the thread being connected by means of a first knot on the first face and a second knot on the second face.

According to preferred but not restrictive variations of the invention, the device is such that:
at least three through holes are aligned,
the support element is circular,
at least three holes are aligned on the diameter of the support element,
the support element has an elongated shape,
at least three holes are aligned on the diameter of the support element,
the support element has a central hole and two peripheral holes,
the central hole is positioned at the centre of the support element,
the two peripheral holes are equidistant from the central hole,
the arrangement of the first knot and the second knot ensures that the thread is held at the level of the first face and the second face respectively,
the first knot consists of a simple knot involving a length of the thread passing through the first peripheral hole and a length passing through the second peripheral hole, a length of thread passing around a free end of the thread on the side of the first face, a length of thread passing under the length of thread around the free end of the thread on the first face side,
the second knot consists of a length of the thread passing through the central hole towards the second face, a length of the thread passing around the length of the thread forming a bridge on the second face.

The present invention also concerns a process for the manufacture of a surgical retaining device characterised in that it includes the following stages:
creation of a bridge on the first face between the two peripheral holes by successive passages of the thread through the first peripheral hole of the first face towards the second face then through the second peripheral hole of the second face towards the first face,
creation of a first knot on the first face,
passing the thread through the central hole of the first face towards the second face,
creation of the second knot on the second face by a complete turn around the bridge of the second face.

BRIEF DESCRIPTION OF THE DRAWING FIGURES

FIGS. 3 to 5 and 9 to 11 show the formation of the first knot.

FIGS. 6 to 8 and 12 to 14 show the formation of the second knot.

FIGS. 3 to 6 and 9 to 12 show the support element with the first face upwards. Whereas FIGS. 7, 8 and 13, 14 show a reverse-side view of the support element with the first face downwards.

FIG. 15 is a perspective view.

FIG. 16 is a front view.

FIG. 17 is a view on section AA of FIG. 16.

DETAILED DESCRIPTION OF THE INVENTION

The remainder of the description employs the term "thread" and "button" but without this being restrictive. These terms may be more generally referred to as "linking element" and "support element".

Figure 1:
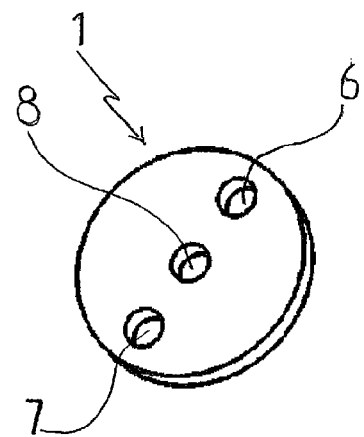
FIG. 1 is a front view of the support element according to the invention.
Figure 2:
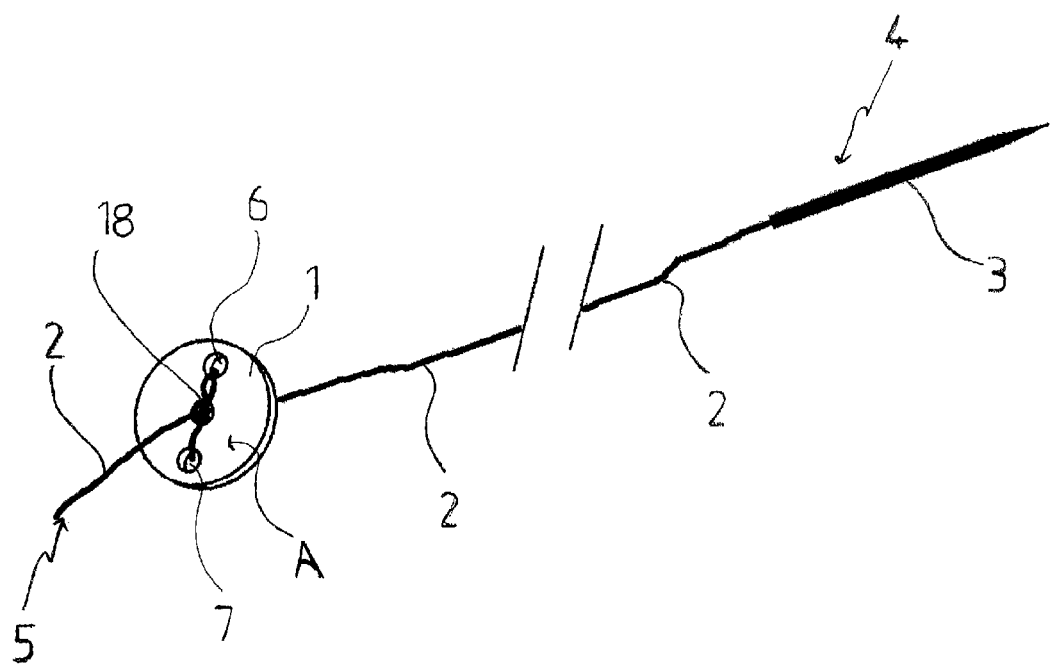
FIG. 2 is a view of the surgical retaining device according to the invention.
Figure 3:
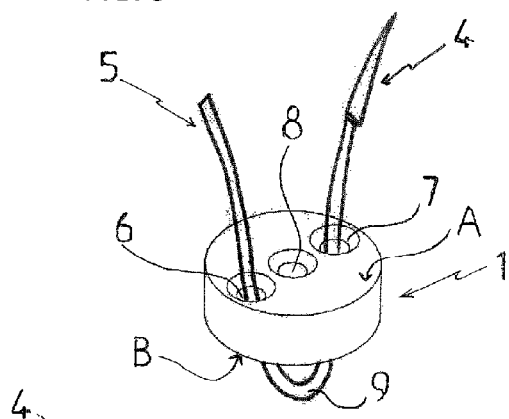
FIGS. 3 to 8 show the different stages in the process for fabrication of the surgical device according to FIG. 2.
Figure 4:
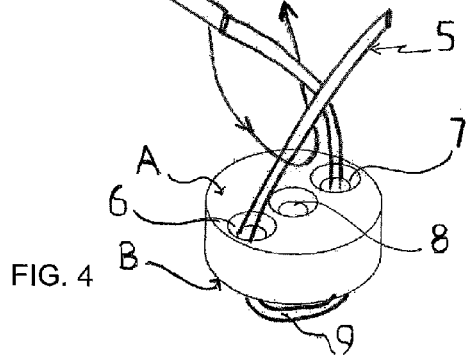
Figure 5:
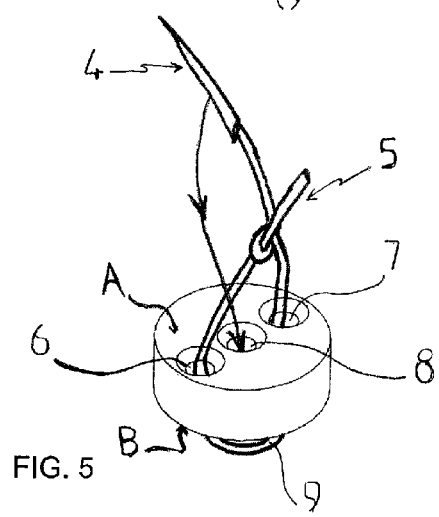

As shown in FIG. 2, the surgical retraction device comprises two main components, a linking element consisting preferably of a thread 2 and a support element consisting preferably of a button 1.

Thread 2 is preferably TEFLON® (polytetrafluoroethylene)-treated polyester braid that will limit the 5 frictional forces.

Button 1 is manufactured preferably from silicone. Button 1 comprises a first face A and the second face B.

Characteristically, button 1 has at least three through holes 6, 7, 8 allowing the passage of thread 2. According to another embodiment, button 1 has more than three holes. Thread 2 passes advantageously through the different holes 6, 7, 8 of button 1 so as to form a first knot 18 on first face A of the button and a second knot 19 on the second face B of button 1. This ensures that thread 2 is joined to button 1.

In a preferred arrangement, thread 2 is equipped with a needle 3 at one of its ends. This needle pierces the abdominal wall; the thread is then secured outside the body of the patient and the biological and/or synthetic tissues can be retracted using the surgical device according to the invention. On the other end, equipped with needle 3 (needled end 4), thread 2 has a free end 5.

Other embodiments may be envisaged. In particular, instead of using a thread 2 equipped with a needle 3, electromagnetic means placed on both button 1 and on a complementary element may be proposed. Button 1 and the additional element are arranged on either side of the biological and/or synthetic tissue to be retracted. Button 1 is preferably placed on the inner face of the tissue to be retracted so that a practitioner may retract the tissue by applying tension to the thread. Therefore, fastening means may also be provided, such as miniature forceps.

In an advantageous arrangement, the three holes 6, 7, 8 are aligned.

Button 1 may be circular as shown on all the figures. In this case, the three holes 6, 7, 8 are aligned preferably across a diameter of button 1.

According to another possibility not shown, button 1 is elongated in an ovoid shape to allow better use during operations involving small diameter trocars. According to this arrangement, the three holes 6, 7, 8 are aligned preferably on the longitudinal axis of button 1.

This alignment of the three holes 6, 7, 8 allows advantageous execution of first knot 18 and second knot 19 roughly in the centre of button 1, thereby centring thread 2, and in particular its needled end 4 to enable correct application of button 1 on the biological and/or synthetic tissue to be retracted.

The three aligned holes 6, 7, 8 consist preferably of central hole 8 and two peripheral holes 6, 7. In an advantageous arrangement, central hole 8 is situated in the centre of button 1. By "centre" is meant the centre of a circular button 1 or, if its shape is different, the centre of gravity of button 1.

According to a preferred embodiment, the three holes 6, 7, 8 are arranged symmetrically across the diameter of button 1 or on its longitudinal axis.

The applicant has observed that the embodiment in which the two peripheral holes 6, 7 are equidistant from central hole 8 allows satisfactory equilibrium of button 1 when used as the support element. Indeed, this arrangement enables balanced positioning of first knot 18 and second knot 19.

First knot 18 is situated on first face A of button 1 and can be made first during the process of fabricating the surgical device according to the invention. First knot 18 is preferably a simple knot. It is made so that it is centred relative to button 1; that is to say, according to certain embodiments, it is positioned roughly at the level of central hole 8.

FIGS. 9, 10 and 11 show stages in making first knot 18. First of all, thread 2 passes through peripheral holes 6, 7 to form a bridge 9 on the second face of button 1. To do this, needled end 4 of thread 2 is preferably inserted through first peripheral hole 6 on first face A in the direction of second face B. Then, threaded end 4 of thread 2 is passed through second peripheral hole 7 of second face B towards first face A.

Two ends 4 and 5 of thread 2 are found at first face A of button 1. These two ends are brought together so as to execute a simple knot. Preferably, needled end 4 is wrapped around free end 5 of thread 2 so as to form a loop 20 through which needled end 4 is inserted and exits loop 20. First knot 18 is tightened by pulling equally on the two ends 4, 5 of thread 2. In a preferred arrangement, knot 18 is positioned at central hole 8. The role of this first knot is to join thread 2 to button 1. It also makes it possible to centre thread 2 at central hole 8 so that a second knot can be created at second face B of button 1 The arrangement of first knot 18 through two peripheral holes 6, 7 also distributes the strain over the entire surface of button 1.

Figure 6:
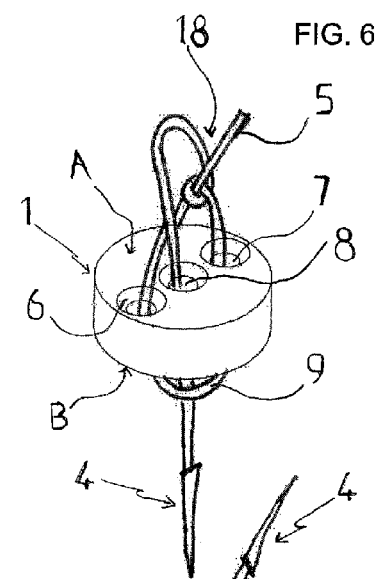
Figure 7:
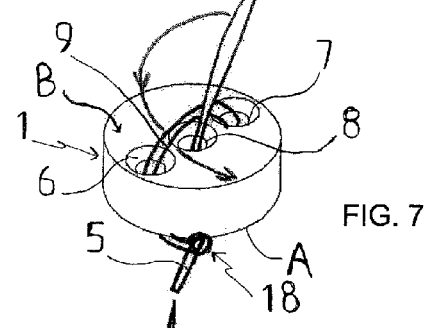
Figure 8:
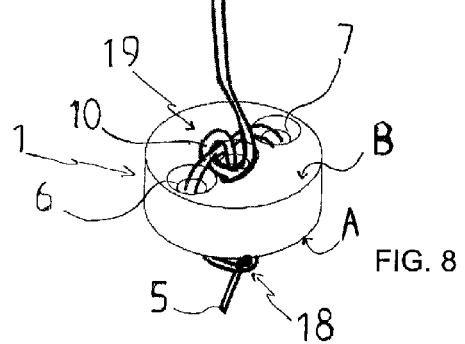
Figure 15:
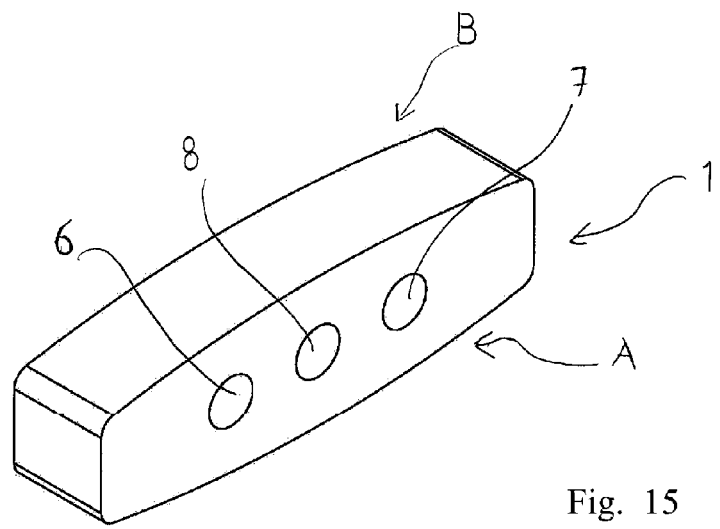
FIGS. 15 to 17 show a support element according to a second embodiment of the invention.
Figure 16:
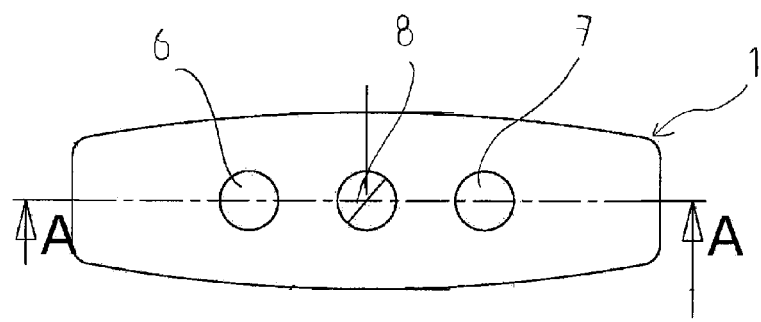
Figure 17:
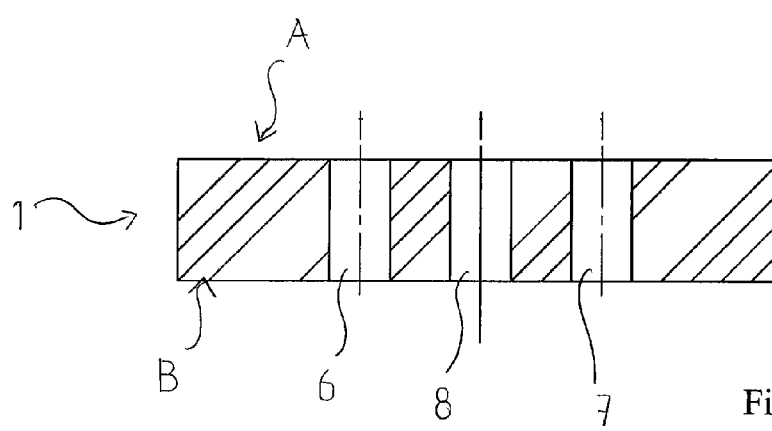

As can be seen in FIG. 6, once first knot 18 has been executed on first face A of button 1, needled end 4 of thread 2 is inserted through central hole 8 of first face A towards second face B. At second face B, needled end 4 will pass successively over bridge 9 then under bridge 9 in order to execute a 360° turn around bridge 9. Second knot 19 enables thread 2 to be blocked on button 1. In fact, during manufacture followed by use, tension is applied to thread 2 through its needled end 4 so as to retighten the first knot and bring bridge 9 closer to the surface of second face B of button 1 so as to press on and block length of thread 22 that is positioned under bridge 9.

Second knot 19 also acts to centre thread 2. In fact, thread 2 exits from central hole 8 of second face B in a central position, second knot 19 holding thread 2 in this central position. This central position of thread 2 relative to button 1 allows button 1 to be correctly positioned when used on biological and/or synthetic tissue.

From a structural standpoint, the first knot consists of a simple knot and includes: a length of thread 11 passing through first peripheral hole 6 of first face A towards second face B, a length of thread 12 forming a bridge 9 on second face B between first peripheral hole 6 and second peripheral hole 7, a portion of thread 13 passing through second peripheral hole 7 of second face B towards first face A, a length of thread 14 passing around loose end 5 of thread 2. This length of thread 14 can be distinguished from a length of thread 23 by passing over free end 5 of thread 2 forming a loop 20 through which passes needled end 4: this is the length of thread 15 positioned under free end 5.

Second knot 19 consists of a length of thread 16 passing through central hole 8 of first face A towards second face B and a length of thread 17 passing around the length of thread 12 forming bridge 9. This length of thread 17 consists of a length of thread 21 situated on the length of thread 12 and a length of thread 22 situated under the length of thread 12.

The surgical fixing device according to the invention may be used in particular for small invasive operations when the surgeon has to operate on a difficult-to-access zone and has to maintain organs retracted from the operation zone. According to a first application, the device enables a thread to be held against biological tissue so as to retract it. The surgeon passes the needle through synthetic tissue such as netting and then through the abdominal wall so as to retract the biological tissue. Button 1 enables the formation of a support zone at the level of the biological and/or synthetic tissue and thread 2 allows tension to be applied in order to maintain the tissue retracted.

According to a variant, the surgeon may use the device according to the invention without any additional element, and to do so will pass needle 3 through biological tissue on which button 1 presses, thereby applying traction to the biological tissue to be retracted by thread 2.

The device according to the invention, especially first knot 18 and second knot 19, enables joint use of thread 2 and button 1 even if thread 2 should break at one of its ends, since it allows the surgeon to recover button 1-thread 2 assembly simultaneously, without any risk of losing the components of the device inside the patient.

The device according to the invention may be radiologically opaque or not, and may be in a material that can be reabsorbed or not.

As an example, a circular type button 1 may be around 9 mm across and 3 mm thick. When the button is elongated, button 1 is around 15 mm long.

In a preferred embodiment, the holes have a diameter of around 1.5 mm. According to an embodiment in which holes 6, 7, 8 are aligned and equidistant, the distance between each hole is around 1.13 mm. The distance will be preferably the same between holes 6 and 7 and the outer edge of button 1. In a preferred arrangement, thread 2 between second knot 19 and its needled end is between 9 and 10 cm long. Needle 3 is preferably 50 mm long.

REFERENCES

1. Support element/Button
2. Thread
3. Needle
4. Needled end
5. Free end
6. $1^{st}$ peripheral hole
7. $2^{nd}$ peripheral hole
8. Central hole
9. Bridge
10. Turn
11. Length of thread passing through $1^{st}$ peripheral hole
12. Length of thread forming a bridge on the second face between $1^{st}$ and $2^{nd}$ peripheral hole
13. Length of thread passing through $2^{nd}$ peripheral hole
14. Length of thread around the free end of the thread
15. Length of thread passing under length of thread 14
16. Length of thread passing through the central hole towards the second face
17. Length of thread commencing the length of thread 12
18. First knot
19. Second knot
20. Loop formed by lengths of thread 11-13 and face A
21. Length of thread situated on length 12
22. Length of thread under length 12
23. Length of thread on free end 5
A. First face
B. Second face

The invention claimed is:

1. A surgical retracting device, comprising:
   a linking element; and
   a support element, wherein
   the linking element is a thread and the support element comprises a first face and a second face and at least three aligned through holes from the first face to the second face in which the thread passes through, the support element and thread being connected by a first knot on the first face and by a second knot on the second face,
   wherein the first knot is formed by passing the thread through a first hole and a second hole of the at least three through holes and the second knot is formed by the successively passing the thread through a third hole of the at least three through holes differing from the first hole and the second hole,
   the at least three holes are aligned and wherein the third hole is a central hole, and the first hole and the second hole are two peripheral holes, the third hole being positioned at the center of the support element,
   the thread is passing only once in each of the first, second and third holes,
   the first knot and second knot are configured in order to maintain a first free end of the thread at a level of the first face and a needle end of the thread at a level of the second face respectively, and
   the first knot comprises a bridge on the second face and the second knot comprises a complete turn around the bridge.

2. The device according to claim 1, wherein the support element is circular.

3. The device according to claim 2, wherein the at least three holes are aligned across a diameter of the support element.

4. The device according to claim 1, wherein the support element is elongated.

5. The device according to claim 4, wherein the at least three holes are aligned across a longitudinal axis of the support element.

6. The device according to claim 5, wherein the two peripheral holes are equidistant from the central hole.

7. The device according to claim 1, wherein the first knot comprises a simple knot comprising a first portion of thread that passes through the first peripheral hole and a second portion of thread that passes through the second peripheral hole to form a bridge on the second face, a third portion of thread passing around a free end of the thread on the side of the first face, a fourth portion of thread passing under the third portion of the thread around the free end of the thread on the first face.

8. The device according to claim 7, wherein the second knot comprises a first portion of thread passing through the central hole towards the second face, a second portion of the thread passing around the first portion of the thread forming a bridge on the second face.

9. A manufacturing process for a surgical fixing device according to claim 7, which comprises the following stages:
   forming a bridge on the first face between the two peripheral holes by successive passages of the thread through the first peripheral hole of the first face towards the second face then through the second peripheral hole of the second face towards the first face;
   forming a first knot on the first face,
   passing thread through the central hole of the first face towards the second face,
   forming the second knot on the second face by a complete turn around the bridge of the second face.

10. The device according to claim 1, wherein the two peripheral holes are equidistant from central hole.

11. The device according to claim 1, wherein the linking element is a polytetrafluoroethylene treated polyester braid.

12. The device according to claim 1, wherein the support element is silicone button.

13. A surgical retracting device, comprising:
- a thread formed from a polytetrafluoroethylene treated polyester braid, one end of the thread being equipped with a 50 mm long needle; and
- a circular silicone button that is about 9 mm across and about 3 mm thick, wherein
- the button comprises a first face and a second face and at least three aligned through holes from the first face to the second face in which the thread passes through, the button and the thread being connected by a first knot on the first face and by a second knot on the second face,
- the first knot is formed by passing the thread through a first hole and a second hole of the at least three through holes and the second knot is formed by the successively passing the thread through a third hole of the at least three through holes differing from the first hole and the second hole,
- the at least three holes are aligned and wherein the third hole is a central hole, and the first hole and the second hole are two peripheral holes, the third hole being positioned at the center of the support element,
- the thread is passing only once in each of the first, second and third holes,
- the first knot and second knot are configured in order to maintain a first free end of the thread at a level of the first face and the needle end of the thread at a level of the second face respectively, and
- the first knot comprises a bridge on the second face and the second knot comprises a complete turn around the bridge.

14. A surgical retracting device, comprising:
- a thread formed from a polytetrafluoroethylene treated polyester braid, one end of the thread being equipped with a 50 mm long needle; and
- an elongated silicone button that is about 15 mm long, wherein
- the button comprises a first face and a second face and at least three aligned through holes from the first face to the second face in which the thread passes through, the button and the thread being connected by a first knot on the first face and by a second knot on the second face,
- wherein the first knot is formed by passing the thread through a first hole and a second hole of the at least three through holes and the second knot is formed by the successively passing the thread through a third hole of the at least three through holes differing from the first hole and the second hole,
- the at least three holes are aligned and wherein the third hole is a central hole, and the first hole and the second hole are two peripheral holes, the third hole being positioned at the center of the support element,
- the thread is passing only once in each of the first, second and third holes,
- the first knot and second knot are configured in order to maintain a first free end of the thread at a level of the first face and the needle end of the thread at a level of the second face respectively, and
- the first knot comprises a bridge on the second face and the second knot comprises a complete turn around the bridge.

\* \* \* \* \*